US006862759B2

(12) United States Patent
Hand et al.

(10) Patent No.: US 6,862,759 B2
(45) Date of Patent: Mar. 8, 2005

(54) HOSPITAL BED (75) Inventors: Barry D. Hand, Mt. Pleasant, SC (US); Dana H. Delk, North Charleston, SC (US); Jack J. Brooks, Folly Beach, SC (US); Steven J. Doehler, Charleston, SC (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 10/379,134

(22) Filed: Mar. 4, 2003

(65) Prior Publication Data
US 2003/0126683 A1 Jul. 10, 2003

Related U.S. Application Data (63) Continuation of application No. 09/701,624, filed as application No. PCT/US99/14525 on Jun. 25, 1999, now Pat. No. 6,526,610.
(60) Provisional application No. 60/090,847, filed on Jun. 26, 1998.

(51) Int. Cl.[7] ............................................. A61G 7/008
(52) U.S. Cl. ........................ 5/430; 5/428; 5/607; 5/658
(58) Field of Search ............................ 5/425, 428, 430, 5/607, 609, 84.1, 86.1

(56) References Cited

U.S. PATENT DOCUMENTS

| 516,614 A | 3/1894 | Seaman |
| 795,155 A | 7/1905 | Nees |
| 1,021,335 A | 3/1912 | Robinson |
| 1,573,571 A | 2/1926 | Pohl |
| 1,667,982 A | 5/1928 | Pearson |
| 1,799,692 A | 4/1931 | Knott |
| 2,076,675 A | 4/1937 | Sharp |
| 2,141,100 A | 12/1938 | Warden |

(List continued on next page.)

FOREIGN PATENT DOCUMENTS

| EP | 0025701 | 3/1981 |
| EP | 0 569 308 A1 | 5/1993 |
| EP | 0 641 545 A1 | 9/1994 |
| FR | 2034679 | 12/1970 |
| FR | 2 247 194 | 5/1975 |
| FR | 2 549 366 | 1/1985 |
| FR | 2 585 240 | 1/1987 |
| FR | 2 587 898 | 4/1987 |
| FR | 2 749 503 | 12/1997 |
| GB | 2 182 570 | 5/1987 |
| WO | WO 93/05745 | 9/1992 |
| WO | WO 97/22323 | 6/1997 |
| WO | WO 98/39996 | 9/1998 |
| WO | WO 99/07320 | 2/1999 |
| WO | WO 99/53997 | 10/1999 |
| WO | WO 00/00117 | 1/2000 |

* cited by examiner

Primary Examiner—Michael Trettel
(74) Attorney, Agent, or Firm—Bose McKinney & Evans LLP (57) ABSTRACT

A patient support includes a base, and a support assembly coupled to the base. A patient support surface is coupled to the support assembly. A plurality of siderails are coupled to the support assembly. Each siderail includes a frame member and a movable member coupled to the frame member, wherein the movable member is movable to a position directly above the patient support surface.

45 Claims, 9 Drawing Sheets

U.S. PATENT DOCUMENTS

| | | | |
|---|---|---|---|
| 2,239,821 A | 4/1941 | Knox | |
| 2,311,542 A | 2/1943 | Holme | |
| 2,391,928 A | 1/1946 | Seib | |
| 2,417,378 A | 3/1947 | Robinson | |
| 2,499,101 A | 2/1950 | Kluglein | |
| 2,503,314 A | 4/1950 | Atwood | |
| 2,607,103 A | 8/1952 | Davidson | |
| 2,613,371 A | 10/1952 | Keyes, Jr. | |
| 2,639,206 A | 5/1953 | Butler | |
| 2,667,169 A | 1/1954 | Kambourakis | |
| 2,673,987 A | 4/1954 | Upshaw et al. | |
| 2,675,564 A | 4/1954 | Hughes | |
| 2,715,737 A | 8/1955 | Sacks | |
| 2,734,104 A | 2/1956 | Gollhofer | |
| 2,803,022 A | 8/1957 | Wynkoop | |
| 2,880,720 A | 4/1959 | Houghtaling | |
| 2,902,701 A | 9/1959 | Driskill | |
| 2,947,007 A | 8/1960 | Oades | |
| 2,984,842 A | 2/1961 | Richards | |
| 3,049,726 A | 8/1962 | Getz | |
| 3,110,912 A | 11/1963 | Propst | |
| 3,111,687 A | 11/1963 | Sacks | |
| 3,151,343 A | 10/1964 | McCormick | |
| 3,200,416 A | 8/1965 | Warrick | |
| 3,206,188 A | 9/1965 | Douglas | |
| 3,210,778 A * | 10/1965 | Robinson | 5/607 |
| 3,226,734 A | 1/1966 | Coventon | |
| 3,238,539 A * | 3/1966 | Koch | 5/607 |
| 3,286,707 A | 11/1966 | Shafer | |
| 3,302,218 A | 2/1967 | Stryker | |
| 3,344,445 A * | 10/1967 | Crawford | 5/430 |
| 3,388,700 A | 6/1968 | Mountz | |
| 3,434,165 A | 3/1969 | Keane | |
| 3,449,776 A | 6/1969 | Brock | |
| 3,451,070 A | 6/1969 | Danielson | |
| 3,499,529 A | 3/1970 | Katzfey et al. | |
| 3,514,794 A | 6/1970 | Pofferi | |
| 3,574,871 A | 4/1971 | Greene | |
| 3,584,321 A | 6/1971 | Buchanan | |
| 3,609,778 A | 10/1971 | Zeiner | |
| 3,647,305 A | 3/1972 | Ersek | |
| 3,653,079 A | 4/1972 | Bourgraf et al. | |
| 3,658,052 A | 4/1972 | Alter | |
| 3,667,075 A | 6/1972 | Ballard | |
| 3,689,945 A | 9/1972 | Laerdal | |
| 3,700,229 A | 10/1972 | Kurokawa et al. | |
| 3,707,734 A | 1/1973 | Matthews | |
| 3,737,924 A | 6/1973 | Davis | |
| 3,739,406 A | 6/1973 | Koetter | |
| 3,748,666 A | 7/1973 | Seng | |
| 3,752,153 A | 8/1973 | Copeland | |
| 3,765,406 A | 10/1973 | Toole et al. | |
| 3,783,863 A | 1/1974 | Kliever | |
| 3,814,414 A | 6/1974 | Chapa | |
| 3,820,176 A | 6/1974 | Feiertag | |
| 3,827,089 A | 8/1974 | Grow | |
| 3,828,377 A | 8/1974 | Eary, Sr. | |
| 3,832,742 A | 9/1974 | Stryker | |
| 3,840,221 A | 10/1974 | Hogan | |
| 3,851,644 A | 12/1974 | Slagle | |
| 3,868,103 A | 2/1975 | Pageot et al. | |
| 3,874,010 A | 4/1975 | Geary | |
| 3,884,225 A | 5/1975 | Witter | |
| 3,890,659 A | 6/1975 | Staubs | |
| 3,902,204 A * | 9/1975 | Lee | 5/86.1 |
| 3,905,591 A | 9/1975 | Schorr et al. | |
| 3,926,181 A | 12/1975 | Eischen | |
| 3,940,808 A | 3/1976 | Petrini | |
| 3,941,365 A | 3/1976 | Frymoyer | |
| 4,017,737 A | 4/1977 | Hudson et al. | |
| 4,024,861 A | 5/1977 | Vincent | |
| 4,030,719 A | 6/1977 | Gabriele et al. | |
| 4,033,000 A | 7/1977 | Bonifay | |
| 4,054,960 A | 10/1977 | Pettit et al. | |
| 4,071,916 A | 2/1978 | Nelson | |
| 4,080,673 A | 3/1978 | Weisler | |
| 4,084,274 A | 4/1978 | Willis et al. | |
| 4,109,329 A | 8/1978 | Tupper | |
| 4,152,795 A | 5/1979 | Rodosta et al. | |
| 4,156,815 A | 5/1979 | Hogan | |
| 4,175,550 A | 11/1979 | Leininger et al. | |
| 4,183,110 A | 1/1980 | Kidd et al. | |
| 4,194,732 A | 3/1980 | Liebman | |
| 4,195,829 A | 4/1980 | Reser | |
| 4,231,030 A | 10/1980 | Weiss | |
| 4,244,358 A | 1/1981 | Pyers | |
| 4,252,594 A | 2/1981 | Cooper | |
| 4,259,950 A | 4/1981 | Klippel | |
| 4,274,167 A | 6/1981 | Immel | |
| 4,277,857 A | 7/1981 | Svehaug | |
| 4,301,791 A | 11/1981 | Franco, III | |
| 4,347,635 A | 9/1982 | Eisenhauer | |
| 4,356,577 A | 11/1982 | Taylor et al. | |
| 4,369,982 A | 1/1983 | Hein et al. | |
| 4,384,378 A * | 5/1983 | Getz et al. | 5/86.1 |
| 4,395,786 A | 8/1983 | Casey et al. | |
| 4,432,353 A | 2/1984 | Vrzalik | |
| 4,473,912 A | 10/1984 | Scheidel et al. | |
| 4,480,345 A | 11/1984 | Dunn | |
| 4,490,867 A | 1/1985 | Gabrielsson | |
| 4,506,664 A | 3/1985 | Brault | |
| 4,533,726 A | 8/1985 | Myers | |
| 4,535,762 A | 8/1985 | Natchev | |
| 4,557,471 A | 12/1985 | Pazzini | |
| 4,558,857 A | 12/1985 | Heller | |
| 4,566,445 A | 1/1986 | Jelsma et al. | |
| 4,572,493 A | 2/1986 | Hubert | |
| 4,578,833 A | 4/1986 | Vrzalik | |
| 4,579,111 A | 4/1986 | Ledesma | |
| 4,584,729 A | 4/1986 | Roberts et al. | |
| 4,584,989 A | 4/1986 | Stith | |
| 4,586,492 A | 5/1986 | Manahan | |
| 4,593,264 A | 6/1986 | Engle | |
| 4,596,384 A | 6/1986 | Blosser | |
| 4,601,075 A | 7/1986 | Smith | |
| 4,612,678 A | 9/1986 | Fitsch | |
| 4,619,270 A | 10/1986 | Margolis et al. | |
| 4,638,516 A | 1/1987 | Vrzalik | |
| 4,655,206 A | 4/1987 | Moody | |
| 4,658,450 A | 4/1987 | Thompson | |
| 4,660,236 A | 4/1987 | Peterson | |
| 4,685,159 A | 8/1987 | Oetiker | |
| 4,763,643 A | 8/1988 | Vrzalik | |
| 4,769,584 A | 9/1988 | Irigoyen et al. | |
| 4,779,858 A | 10/1988 | Saussereau | |
| 4,811,435 A | 3/1989 | Foster et al. | |
| 4,827,541 A | 5/1989 | Vollman et al. | |
| 4,840,362 A | 6/1989 | Bremer et al. | |
| 4,841,585 A | 6/1989 | Masuzawa | |
| 4,847,929 A | 7/1989 | Pupovic | |
| 4,852,193 A | 8/1989 | Alsip et al. | |
| 4,856,128 A | 8/1989 | Alsip et al. | |
| 4,866,796 A | 9/1989 | Robinson et al. | |
| 4,868,937 A | 9/1989 | Connolly | |
| 4,872,657 A | 10/1989 | Lussi | |
| 4,873,710 A | 10/1989 | Lotman | |
| 4,873,731 A | 10/1989 | Williamson | |
| 4,895,173 A | 1/1990 | Brault et al. | |
| 4,912,754 A | 3/1990 | Van Steenburg | |
| 4,920,589 A | 5/1990 | LaVelle et al. | |
| 4,924,537 A | 5/1990 | Alsip et al. | |

| Patent No. | Date | Inventor |
|---|---|---|
| 4,939,801 A | 7/1990 | Schaal et al. |
| 4,941,221 A | 7/1990 | Kanzler |
| 4,944,054 A | 7/1990 | Bossert |
| 4,947,418 A | 8/1990 | Barr et al. |
| 4,947,496 A | 8/1990 | Connolly |
| 4,951,032 A | 8/1990 | Langsam |
| 4,958,817 A | 9/1990 | Heller et al. |
| 4,960,271 A | 10/1990 | Sebring |
| 4,970,739 A | 11/1990 | Bradford |
| 4,987,622 A | 1/1991 | Shockey |
| 4,988,062 A * | 1/1991 | London .................... 248/68.1 |
| 5,005,233 A | 4/1991 | Toivio et al. |
| 5,014,374 A | 5/1991 | Williams |
| 5,016,268 A | 5/1991 | Lotman |
| 5,018,712 A | 5/1991 | Schaefer |
| 5,020,170 A | 6/1991 | Ruf |
| 5,023,968 A * | 6/1991 | Diehl et al. ................ 5/81.1 R |
| 5,048,071 A | 9/1991 | Van Steenburg |
| 5,048,134 A | 9/1991 | Dennill et al. |
| 5,060,324 A | 10/1991 | Marinberg et al. |
| 5,062,171 A | 11/1991 | Vrzalik |
| 5,073,999 A | 12/1991 | Thomas et al. |
| 5,083,574 A | 1/1992 | Schlutow |
| 5,088,137 A | 2/1992 | Rose |
| 5,088,706 A | 2/1992 | Jackson |
| 5,092,007 A | 3/1992 | Hasty |
| 5,103,511 A | 4/1992 | Sequin |
| 5,121,514 A | 6/1992 | Rosane |
| 5,121,756 A | 6/1992 | Koledin |
| 5,127,422 A | 7/1992 | Colon |
| 5,131,103 A | 7/1992 | Thomas et al. |
| 5,131,105 A | 7/1992 | Harrawood et al. |
| 5,131,106 A | 7/1992 | Jackson |
| 5,148,815 A | 9/1992 | Britton |
| 5,152,024 A | 10/1992 | Chrones et al. |
| 5,154,185 A | 10/1992 | Latimer et al. |
| 5,154,186 A | 10/1992 | Laurin et al. |
| 5,159,312 A | 10/1992 | Engle |
| 5,179,746 A | 1/1993 | Rogers |
| 5,181,288 A | 1/1993 | Heaton et al. |
| 5,190,056 A | 3/1993 | Hull |
| 5,208,928 A | 5/1993 | Kuck et al. |
| 5,211,186 A | 5/1993 | Shoemaker et al. |
| 5,230,112 A | 7/1993 | Harrawood et al. |
| 5,230,113 A | 7/1993 | Foster et al. |
| 5,243,639 A | 9/1993 | Johnson |
| 5,249,318 A | 10/1993 | Loadsman |
| 5,250,802 A | 10/1993 | Runner |
| 5,255,303 A | 10/1993 | DiMaio et al. |
| 5,263,213 A | 11/1993 | Robertson et al. |
| 5,274,862 A | 1/1994 | Palmer, Jr. et al. |
| 5,274,864 A | 1/1994 | Morgan |
| 5,285,797 A | 2/1994 | Zeller |
| 5,299,334 A | 4/1994 | Gonzalez |
| 5,319,817 A | 6/1994 | Hay et al. |
| 5,334,186 A * | 8/1994 | Alexander .................. 604/180 |
| 5,336,179 A * | 8/1994 | Ryan .......................... 604/80 |
| 5,345,630 A | 9/1994 | Healy |
| 5,396,673 A | 3/1995 | Foster |
| 5,398,356 A | 3/1995 | Pfleger |
| 5,404,603 A | 4/1995 | Fukai et al. |
| 5,412,823 A | 5/1995 | Sitta |
| 5,414,883 A | 5/1995 | Fangrow, Jr. |
| 5,418,990 A | 5/1995 | Risasen |
| 5,425,148 A | 6/1995 | Ashcraft et al. |
| 5,427,338 A | 6/1995 | Garrett et al. |
| 5,433,741 A | 7/1995 | Truglio |
| 5,435,323 A | 7/1995 | Rudy |
| 5,473,784 A | 12/1995 | Nixon et al. |
| 5,481,770 A | 1/1996 | Ahlsten |
| 5,494,051 A | 2/1996 | Schneider, Sr. |
| 5,497,097 A | 3/1996 | Walling et al. |
| 5,499,416 A | 3/1996 | Daouk |
| 5,502,853 A | 4/1996 | Singleton et al. |
| 5,502,854 A | 4/1996 | Daouk |
| 5,515,561 A | 5/1996 | Suggitt et al. |
| 5,515,869 A | 5/1996 | Powell et al. |
| 5,530,974 A | 7/1996 | Rains et al. |
| 5,560,059 A | 10/1996 | McQueen |
| 5,568,662 A | 10/1996 | Gougelet |
| 5,577,281 A | 11/1996 | Mital et al. |
| 5,611,096 A | 3/1997 | Bartlett et al. |
| 5,621,932 A | 4/1997 | Strachan |
| 5,621,933 A | 4/1997 | Knapp et al. |
| 5,625,913 A * | 5/1997 | Singleton ..................... 5/609 |
| 5,626,150 A | 5/1997 | Johnson et al. |
| 5,664,270 A | 9/1997 | Bell et al. |
| 5,699,568 A | 12/1997 | Couldridge |
| 5,740,571 A | 4/1998 | Tyra |
| 5,769,797 A | 6/1998 | Van Brunt et al. |
| 5,790,996 A | 8/1998 | Narfstrom |
| 5,860,899 A | 1/1999 | Rassman |
| 5,864,901 A | 2/1999 | Blumel |
| 5,966,762 A | 10/1999 | Wu |
| 6,012,183 A | 1/2000 | Brooke et al. |
| 6,021,533 A | 2/2000 | Ellis et al. |
| 6,030,353 A | 2/2000 | Van Brunt |
| 6,036,662 A | 3/2000 | Van Brunt et al. |
| 6,065,165 A | 5/2000 | Delk et al. |
| 6,108,838 A | 8/2000 | Connolly et al. |
| 6,112,349 A * | 9/2000 | Connolly ..................... 5/607 |
| 6,119,292 A | 9/2000 | Haas |
| 6,141,806 A | 11/2000 | Bobey et al. |
| 6,155,996 A | 12/2000 | Van Brunt et al. |
| 6,240,584 B1 | 6/2001 | Perez et al. |
| 6,260,220 B1 | 7/2001 | Lamb et al. |
| 6,282,736 B1 | 9/2001 | Hand et al. |
| 6,308,353 B1 | 10/2001 | Van Steenburg |
| 6,327,727 B1 | 12/2001 | Bocharnikov |
| 6,340,025 B1 | 1/2002 | Van Brunt |
| 6,353,949 B1 | 3/2002 | Falbo |
| 6,375,017 B1 | 4/2002 | Schattner et al. |
| 6,379,316 B1 | 4/2002 | Van Brunt et al. |
| 6,385,801 B1 | 5/2002 | Watanabe et al. |
| 6,415,791 B1 | 7/2002 | Van Brunt |
| 6,471,663 B1 | 10/2002 | Van Brunt et al. |
| 6,499,160 B2 | 12/2002 | Hand et al. |
| 6,526,610 B1 * | 3/2003 | Hand et al. .................... 5/607 |
| 6,609,260 B2 | 8/2003 | Hand et al. |
| 2002/0026671 A1 | 3/2002 | Hand et al. |
| 2003/0126683 A1 | 7/2003 | Hand et al. |

HOSPITAL BED

CROSS-REFERENCE TO RELATED APPLICATIONS

This application is a continuation of U.S. patent application Ser. No. 09/701,624, filed Dec. 1, 2000, now U.S. Pat. No. 6,526,610, which claims priority to PCT International Patent Application No. PCT/US99/14525, filed Jun. 25, 1999, which claims the benefit of U.S. Provisional Patent Application Ser. No. 60/090,847, filed Jun. 26, 1998, all of which are expressly incorporated herein by reference.

BACKGROUND AND SUMMARY OF THE INVENTION

The present invention relates to a hospital bed. More particularly, the present invention relates to a hospital bed including a plurality of siderails movable relative to a patient support surface of the bed.

A bed of the present invention illustratively includes a base, and a support assembly coupled to the base. The support assembly includes first and second support arms located above the base. The apparatus also includes a plurality of latch mechanisms coupled to the first and second support arms, and a patient support surface configured to be coupled to the first and second support arms by the plurality of latch mechanisms. The patient support surface is removable from the first and second support arms to permit transfer of a patient to and from the bed on the patient support surface.

In an illustrated embodiment, the support assembly is coupled to a first end of the base. The support assembly includes a rotatable drive mechanism coupled to the first and second support arms for rotating the first and second arms about a longitudinal axis. The first and second support arms may be cantilevered from the support assembly or coupled to a support located at the end of the second base.

A proning surface is configured to be coupled to the first and second support arms. The proning surface is configured to support the patient in a prone position when the patient support assembly is rotated 180° about its longitudinal axis by the drive mechanism. In an illustrated embodiment, a plurality of siderails is coupled to the first and second support arms. The siderails each include a portion which is movable over the patient support surface to form a portion of the proning surface.

The illustrated patient support surface includes an outer frame configured to be coupled to the plurality of latch mechanisms to secure the patient support surface to the first and second support arms. The patient support surface also includes a plurality of panels coupled to the outer frame. The panels illustratively include notched portions configured to define handles on the patient support surface. The plurality of panels is pivotably coupled to the outer frame.

The illustrated patient support surface further includes at least one hinge to permit articulation of the patient support surface. The patient support surface includes at least one locking member configured to block pivotal movement of the hinge to hold the patient support surface in a generally planar orientation. The support assembly includes an actuator for selectively releasing the locking member to permit articulation of the patient support surface. In an illustrated embodiment, a latching mechanism is configured to engage each locking member. The actuator is configured to move the latching mechanism relative to the first and second support arms to expose the hinge and permit articulation of the patient support surface.

The illustrated embodiment of the present invention includes a transfer surface coupled to the base. The transfer surface is movable from a lowered position to an elevated position located adjacent the first and second support arms when the patient support surface is coupled to and removed from the first and second support arms. In one embodiment, the transfer surface is configured to engage a portion of the plurality of latch mechanisms as the transfer surface is moved to the elevated position to open the latch mechanisms for receiving the patient support surface.

A line management apparatus of the present invention is configured to be coupled to a patient support surface for routing medical lines and hoses. The apparatus includes a body portion having a top edge. The body portion is formed to include a plurality of notches opening along the top edge to receive the lines and hoses and a plurality of apertures located below the notches for receiving additional lines and hoses. A coupler is coupled to the body portion adjacent to the plurality of apertures. The coupler is configured to connect the body portion to the patient support surface.

In a further illustrated embodiment, a patient support includes a base and a support assembly coupled to the base. A patient support surface is coupled to the support assembly. A plurality of siderails are coupled to the support assembly, each siderail illustratively configured to move between a lowered position and an elevated position. Each siderail includes a frame member and a movable member coupled to the frame member. The movable member is configured to move relative to the frame member to a position directly above the patient support surface when the siderail is in the elevated position. Illustratively, the frame member of each siderail includes a top rail, and the movable member is pivotably coupled to the top rail.

Additional features of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying drawings in which.

DETAILED DESCRIPTION OF THE DRAWINGS

Figure 1:
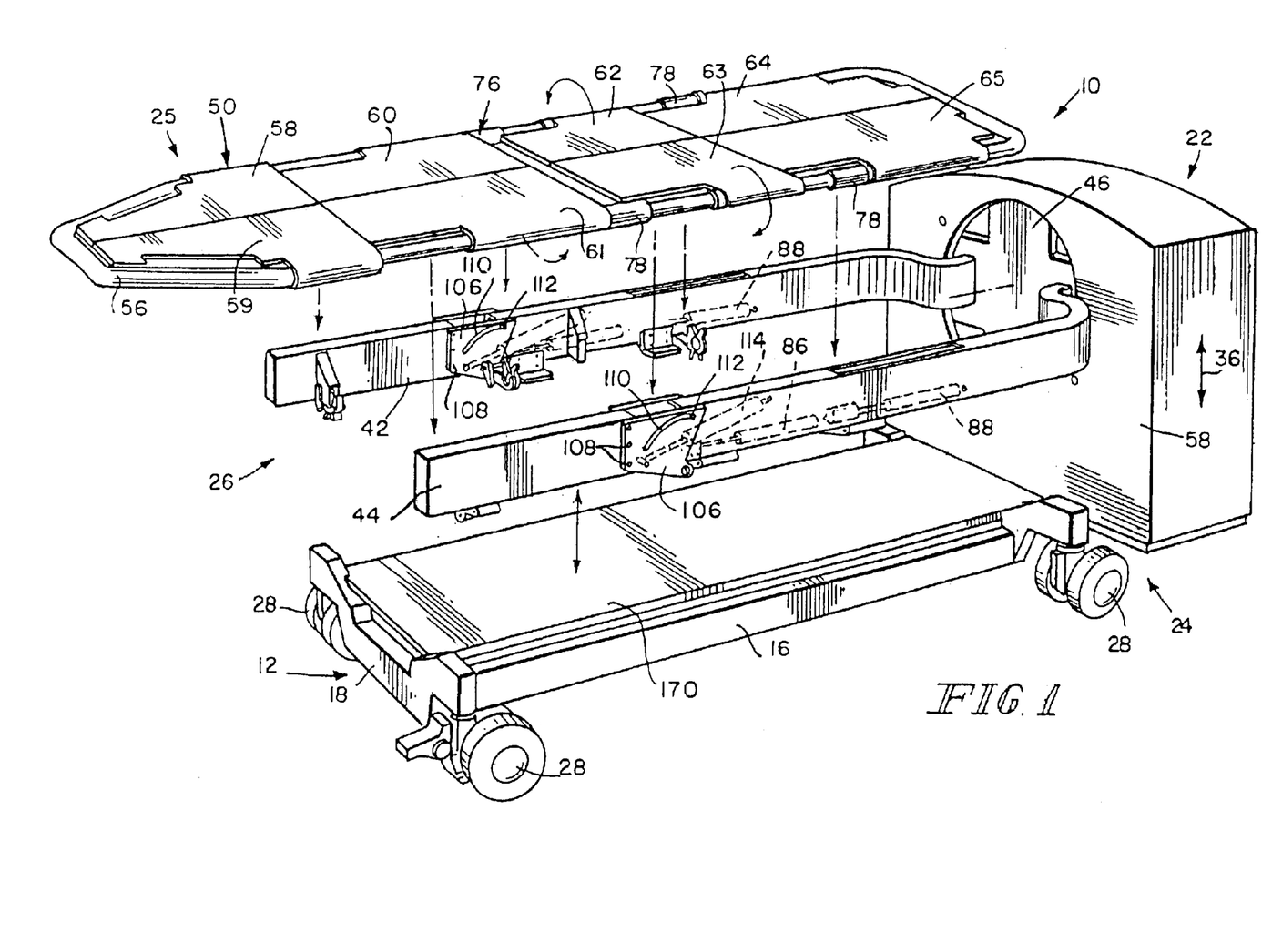
FIG. 1 is an exploded perspective view of a proning bed of the present invention including a patient support surface spaced apart from first and second support arms which are coupled to a rotating support assembly.

Referring now to the drawings, FIG. 1 illustrates a bed 10 having a base 12 which includes opposite side members 14 and 16 and cross members 18 and 20 extending between side members 14 and 16. A support assembly 22 is located at a foot end 24 of bed 10. Support assembly 22 supports a patient support assembly 26 in a cantilevered fashion. Therefore, the head end 25 of bed 10 is open to facilitate access to the patient (not shown). It is understood that in another embodiment of the present invention a support is coupled to the head end of the base 12 for supporting the head end of the patient support assembly 26. Therefore, the present invention is not limited to a cantilevered design.

Support assembly 22 is coupled to base 12. Base 12 is supported by casters 28 which are illustratively lockable. The support assembly 22 is movable up and down in the direction of double-headed arrow 36 to raise and lower the height of patient support assembly 26. Support assembly 22 can rotate the patient support assembly 26 about its longitudinal axis 38 as indicated by double-headed arrow 40. Support assembly 22 can rotate the patient support assembly 26 in either direction a full 360°. In other words, the patient can be rotated 180° to prone the patient to aid with respiratory disorders such as ARDS, or in order to perform surgical procedures or to permit the patient to lie face down on the support surface. The present invention permits full 180° rotation of a patient located on a patient support surface while providing spinal stability for spinal trauma patients. A proning surface (not shown in FIGS. 1 and 2) is attached to the patient support assembly 26 before the patient support assembly 26 is rotated.

Patient support assembly 26 includes a pair of horizontally extending support arms 42 and 44 which are coupled to a cruciform-shaped plate 46 of support assembly 22. In the illustrated embodiment, the arms 42 and 44 extend away from support assembly 22 in a cantilevered fashion. A patient support surface 50 is coupled between arms 42 and 44 as discussed below.

Cruciform 46 is coupled to a rotatable, annular rack which is held in place on a front surface 58 of support assembly 22 of rotatable bearings which are also coupled to front surface 58. Cruciform 46 includes four arms which are each secured to the annular rack. A motor and gear are located on support assembly 22. The gear engages the annular rack to rotate the annular rack relative to the front surface 58. Therefore, the support arms 42 and 44 coupled to the cruciform also rotate in the direction of double-headed arrow 40 in FIG. 2. Details of the support assembly 22 are described in PCT International Publication No. WO 99/07320 which is incorporated herein by reference.

Patient support surface 50 includes an outer frame 56 and the plurality of panels 58–65 which are pivotably coupled to the outer support frame 56 by pivot connections 66. In the illustrated embodiment, the panels 58–65 are all pivotable upwardly or downwardly about opposite sides of outer frame 56. This pivotable movement of panels 58–65 provides access to the patient when in the prone position. Portions of panels 58–65 are spaced apart from outer frame 56 to provide hand access for gripping the patient support surface 50 during transport. In other words, apertures or notches in panels 58–65 define grip locations 68 for the patient support surface 50.

Figure 3:
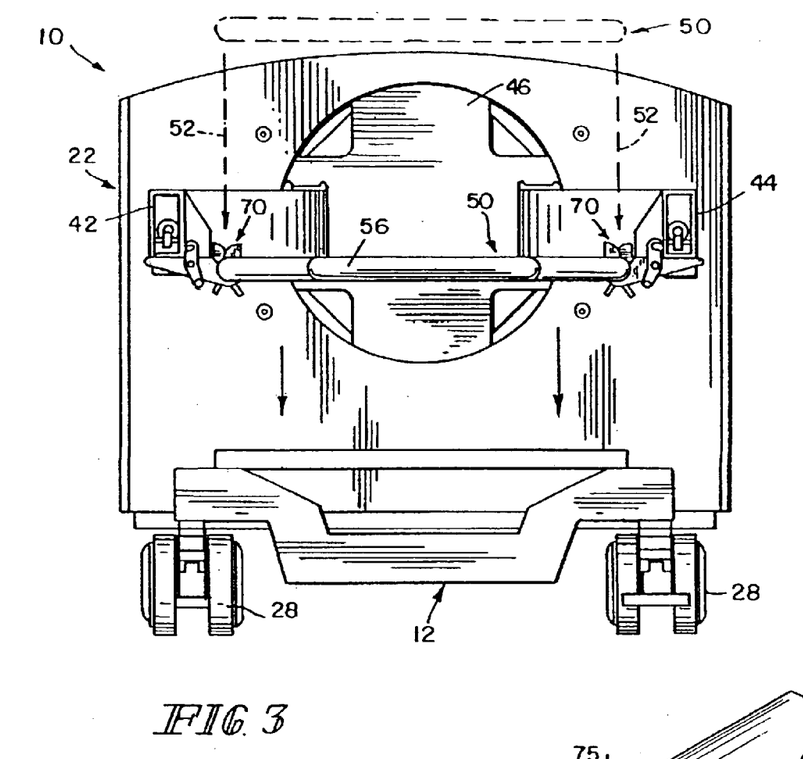
FIG. 3 is an end view of the bed of FIGS. 1 and 2 illustrating coupling of the patient support surface to the first and second support arms by latch mechanisms.

The patient support surface 50 is designed for use in the field at an injury location for transporting a patient in the manner of a backboard or stretcher. The support surface 50 is then loaded into the bed 10 without having to move the patient off of the surface 50. Bed 10 includes latching mechanisms 70, 72, and 74 for a head panel, seat panel, and leg panel, respectively, of the patient support surface 50. When the patient support surface 50 is brought to the bed 10, it is lowered between the side arms 42 and 44 as shown in arrows 52 in FIG. 3 and automatically latched by the latching mechanisms 70, 72, and 74 which engage the outer frame member 56 as discussed below.

Figures 4, 6:
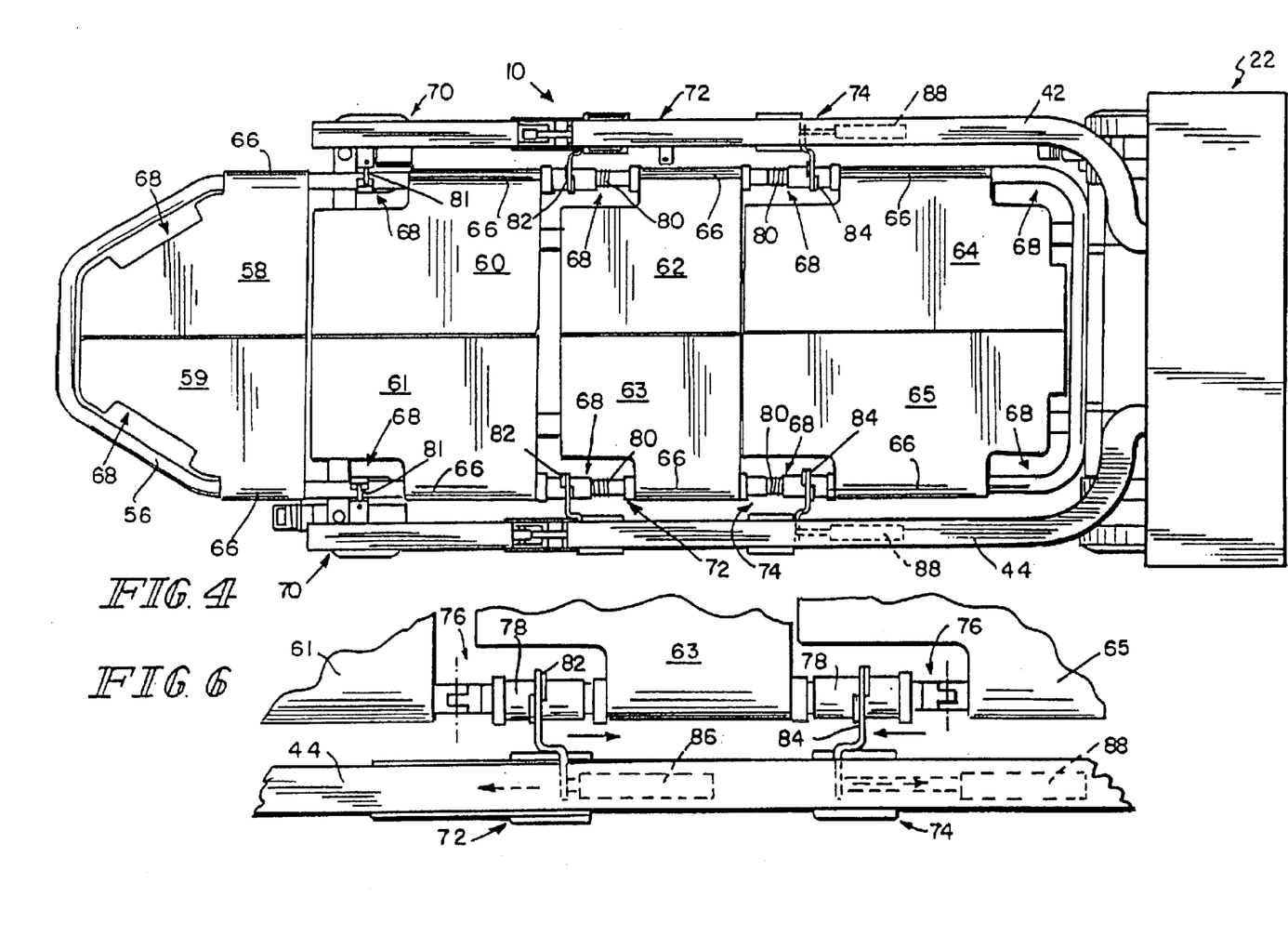
FIG. 4. is a top plan view of the bed of FIG. 2.
FIG. 6 is a partial view of the bed of FIG. 4 illustrating movement of first and second latch mechanisms to move the locking cylinders away from the hinges to permit articulation of the patient support surface.
Figure 5:
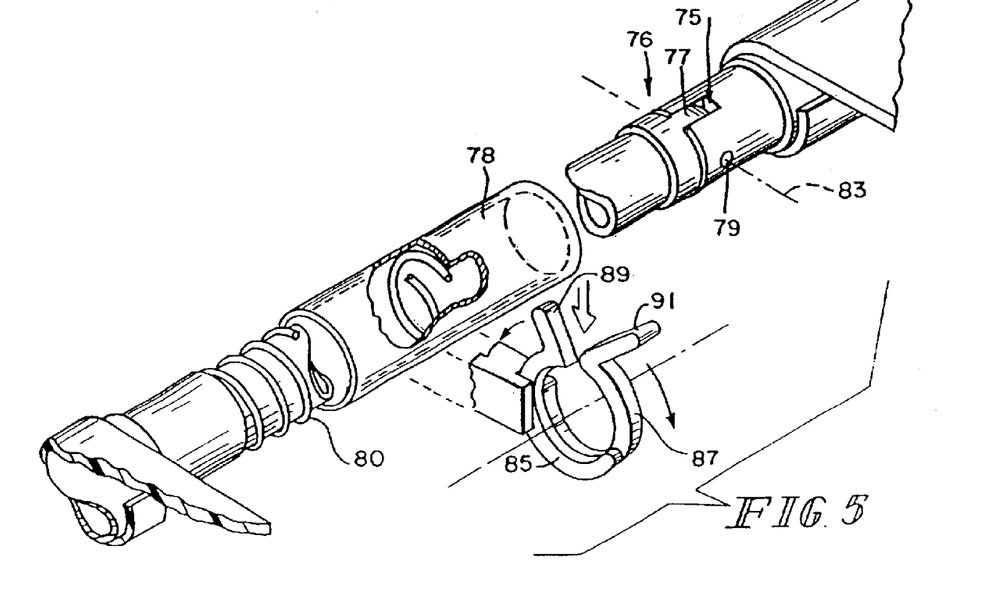
FIG. 5 is an exploded perspective view illustrating details of a hinge of the patient support surface, a locking cylinder movable on an outer frame of the patient support surface for blocking articulation of the patient support surface, and the latch mechanism.

The patient support surface 50 includes hinge connections 76 between the head section which includes panels 58–61 and the seat section which includes panels 62 and 63. Hinge connections 76 are also provided between panels 62 and 63 and the leg section which includes panels 64 and 65. The hinge connections 76 are best illustrated in FIG. 5. The hinge connections 76 are covered with slidable locking cylinders 78 during transport to prevent pivoting movement of the patient support surface 50. The cylinders 78 are shown in a locked position in FIGS. 1, 2 and 4. Illustratively, the locking cylinders 78 are biased to the closed position by springs 80. FIGS. 5 and 6 illustrate cylinders 78 in open positions so that hinges 76 are exposed to permit articulation between adjacent head, seat and foot sections of patient support surface 50.

Figure 10:
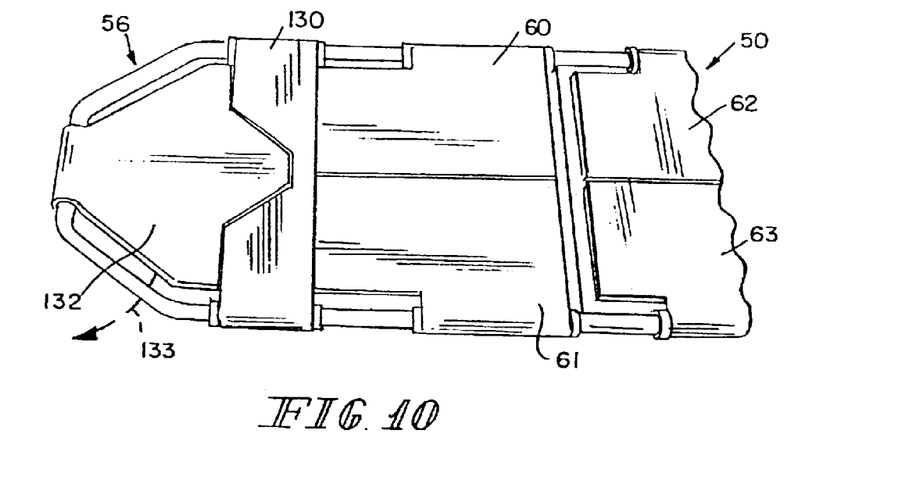
FIG. 10 is a perspective view of another patient support surface of the present invention.

Patient support surface 50 is loaded into the bed 10 with cylinders 78 in the locked position. As shown in FIG. 10, latches 81 of latch mechanism 70 engage a portion of the outer frame 56. Latches 82 of latch mechanisms 72 engage the cylinders 78 between head and seat sections of the patient support 50. Latches 84 of latch mechanisms 74 engage the cylinders 78 between the seat section and foot sections of patient support surface 50. Hydraulic cylinders 86 and 88 are coupled to latch mechanisms 72 and 74, respectively, as best shown in FIG. 6. Cylinders 86 and 88 are located within frame members 42 and 44 on each side of the bed 10. Cylinders 86 are actuated to move the latches 82 toward foot end 24 of bed 10. Movement of latches 82 causes movement of locking cylinders 78 away from the hinges 76 located between the head section and the seat section of patient support surface 50 to permit articulation of the head section of the patient support surface 50. Similarly, cylinders 88 are actuatable to move latches 84 toward the head end 25 of bed 10. Such a movement causes the locking cylinders 78 to move toward head end 25 and expose hinges 76 between the seat section and the foot section of the patient support surface 50 to permit articulation of the foot section. Cylinders 86 and 88 can be actuated automatically upon installation of the patient support surface 50 into the bed 10. Otherwise, the cylinders 86 and 88 are actuated only when articulation of the patient support surface 50 is initiated. In this instance, the cylinders 86 and 88 keep the locking cylinders 78 over the hinges 76 until articulation is initiated.

Figure 7:
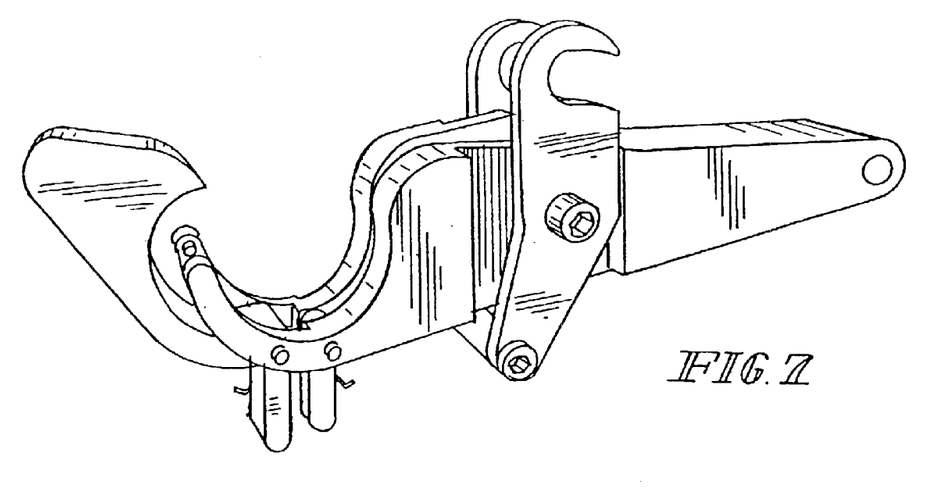
FIGS. 7 and 8 illustrate additional embodiments of latching mechanisms.
Figure 8:
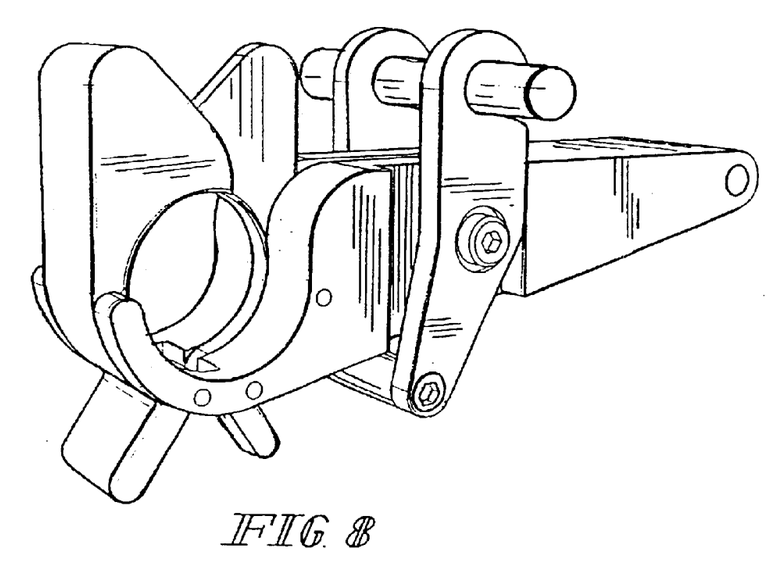

Further details of the hinges 76 are illustrated in FIG. 5. Hinge 76 includes a slot 75 formed in a first portion of frame 56 and a tab 77 formed on a second portion of frame 56. A pivot pin 79 extends through the slot 75 and tab 77 so that the hinge 76 pivots about axis 83. The latches 81, 82 and 84 include first and second latch portions 85 and 87 as shown in FIG. 5. Latch portions 85 and 87 include lead-in ramp surfaces 89 and 91, respectively, so that the latches are automatically opened during insertion of the patient support surface 50. In another embodiment, the latches 81, 82 and 84 are opened by upward movement o the transfer surface 170. Other configurations of the latches 81, 82 and 84 are illustrated in FIGS. 7 and 8.

Figure 2:
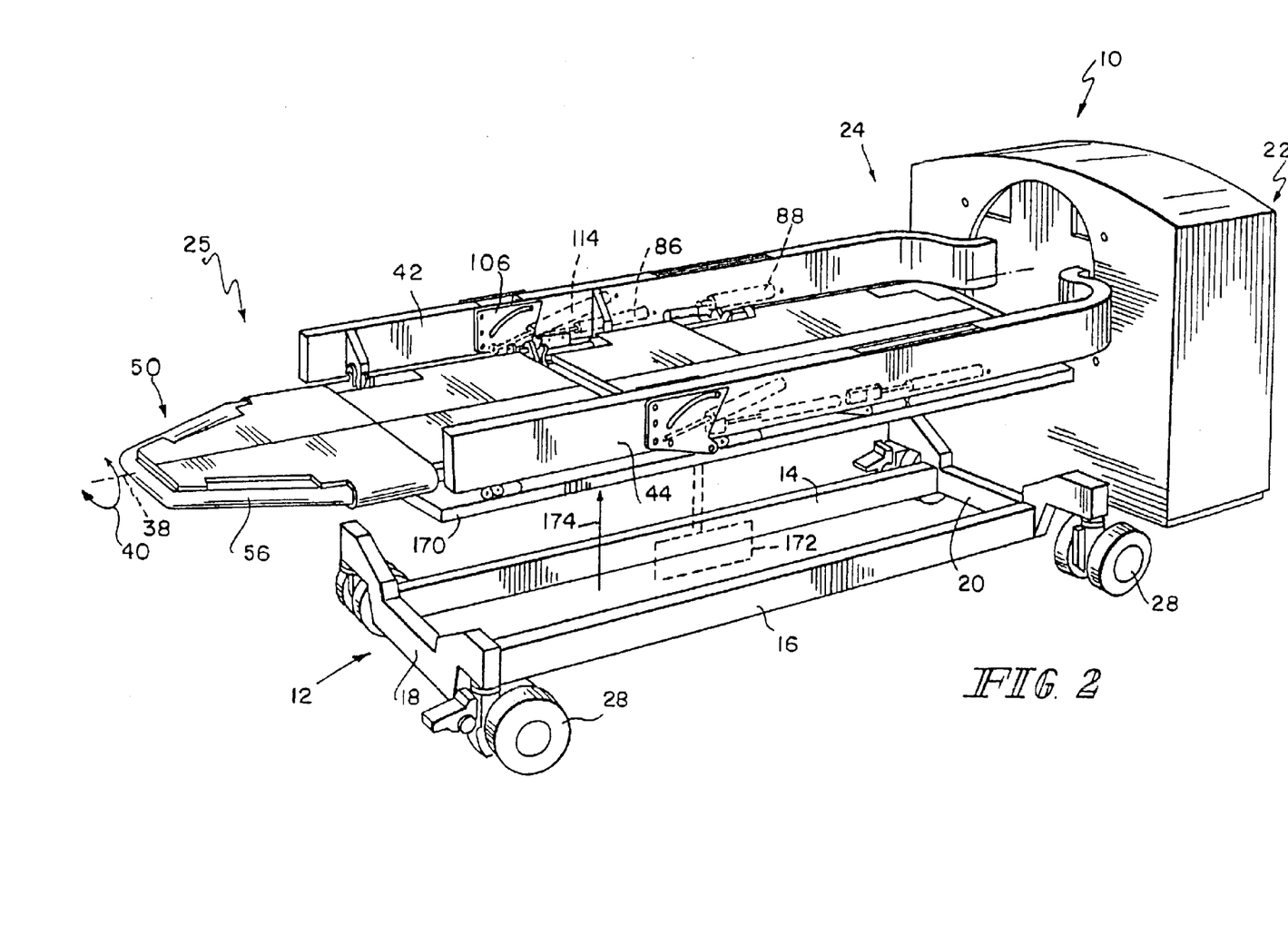
FIG. 2 is a perspective view similar to FIG. 1 in which the patient support surface has been coupled to the first and second support arms.
Figure 9:
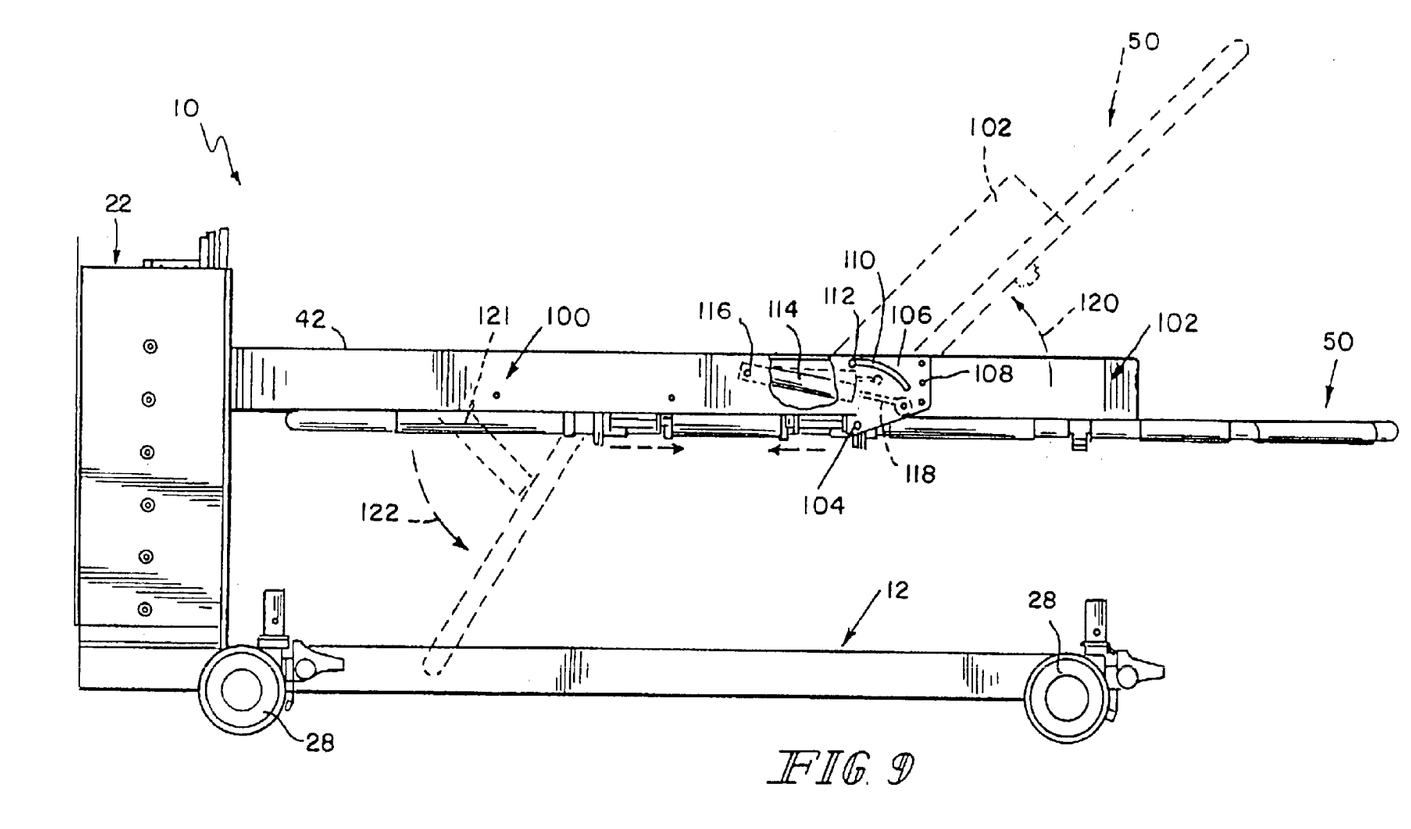
FIG. 9 is a side elevational view illustrating articulation of the first and second support arms and the patient support surface.

As best illustrated in FIGS. 1, 2 and 9, the support arms 42 and 44 each include foot end sections 100 and head end sections 102 which are pivotably coupled to foot end sections 100 by pivot connections 104. Plates 106 are rigidly coupled to head end sections 102 by fasteners 108. Plates 106 are formed to include arcuate slots 110 which slide over pins 112 coupled to foot end sections 100 of arms 42 and 44. Therefore, head end sections 102 can pivot upwardly relative to foot end sections 100 to elevate the head end of the bed.

A cylinder 114 is pivotably coupled to each foot end section 100 of arms 42 and 44 by a pivot connection 116 best shown in FIG. 9. Cylinders 114 include pistons 118 which are pivotably coupled to head end sections 102 of side arms 42 and 44. When the pistons 118 are in the extended position shown in FIG. 9, the head end sections 102 and foot end sections 104 of arms 42 and 44 are generally parallel. When piston 118 is retracted, head end sections 102 pivot upwardly as shown in FIG. 9 to elevate the head end of the bed 10 in the direction of arrow 120 of FIG. 8. An internal frame and drive mechanism 121 is provided to move the leg section patient support surface 50 downwardly in the direction of arrow 122, if desired.

Figure 11:
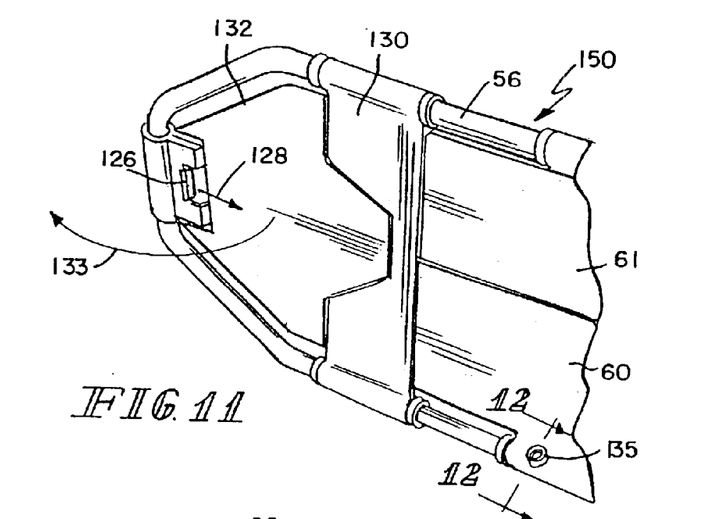
FIG. 11 is a perspective view of the patient support surface of FIG. 10 illustrating latch mechanisms for holding panels of the patient support surface in a generally planar orientation.
Figure 12:
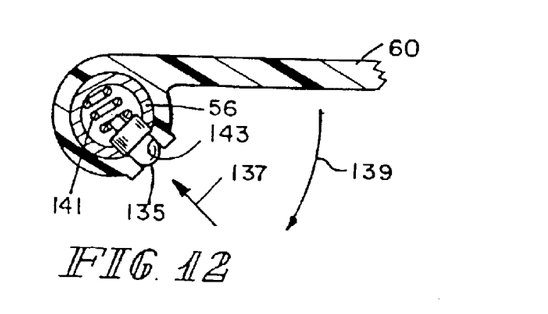
FIG. 12 is a sectional view taken along lines 12—12 of FIG. 11 illustrating details of one of the latch mechanisms.
Figure 13:
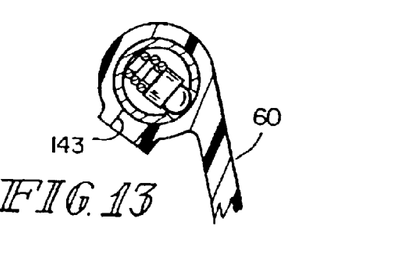
FIG. 13 is a sectional view of the latch mechanism of FIG. 12 which has been actuated to release the panel and permit pivotable movement of the panel relative to the outer frame of the patient support surface.

As discussed above, the panels 58–65 of patient support surface 50 are pivotable relative to the outer frame 56. FIGS. 11 and 12 illustrate another embodiment of a head support mechanism including a fixed member 130 extending between opposite sides of frame 56 and a pivotable head portion 132. Head portion 132 is pivotable outwardly relative to a head end of frame 56 when latch 126 is activated as illustrated by arrow 133. FIG. 11 illustrates a release plate 126 which must be pushed inwardly toward the center of the patient support surface 50 in the direction of arrow 128 in order to release the panel 131 for pivotable movement. This reduces the likelihood that the latch mechanisms 126 will be inadvertently actuated by a caregiver during transport. Another type of release mechanism is a push button release mechanism 135 illustrated in FIGS. 11–13. The push button 135 is located at an angle relative to frame member 56 so that push button 135 is not activated when the patient support surface 50 rests on the ground. Push button 135 is pressed in the direction of arrow 137 to release a panel 60 for pivotable movement in the direction of arrow 139 in FIG. 12. A spring 141 biases the push button 135 to the locking position of FIG. 12 when an aperture 143 formed in panel 60 is aligned with the push button 135. FIG. 13 illustrates the panel 60 in a downwardly pivoted position. It is understood that either type of latch mechanism 126, 135 may be used with any of the panels of the patient support surface 50.

Figure 14:
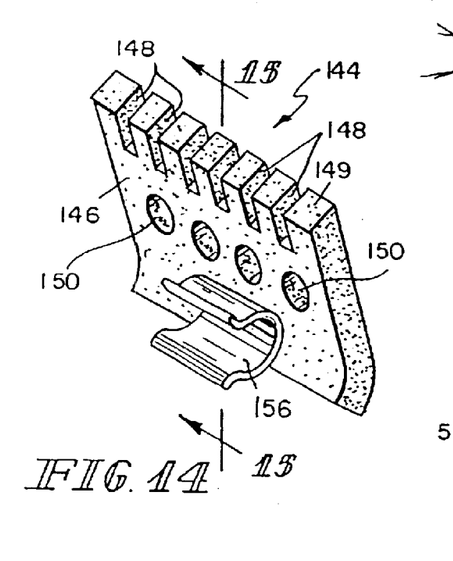
FIG. 14 is a perspective view of a line management apparatus of the present invention configured to be coupled to the outer frame of the patient support surface.
Figure 15:
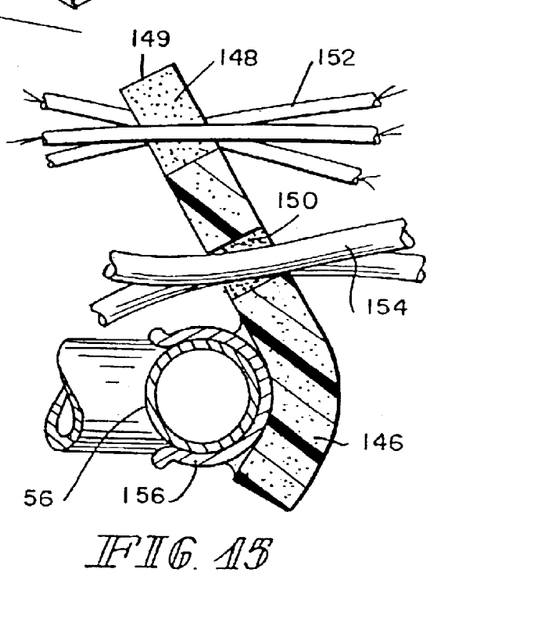
FIG. 15 is a sectional view taken along lines 15—15 of FIG. 14 with the line management apparatus installed on the outer frame of the patient support surface.

FIGS. 14 and 15 illustrate a line management apparatus 144 configured to be coupled to a head end of the outer frame 56. Illustratively, the line management apparatus 144 includes a foam body 146 formed to include top notches 148 adjacent a top edge 149 and apertures 150 for routing IV lines or other hoses/lines 152, 154 to the patient as shown in FIG. 15. A clip 156 is coupled to body 146. Clip 156 is illustratively a C-shaped clip configured to be coupled frame 56.

Figures 16, 17:
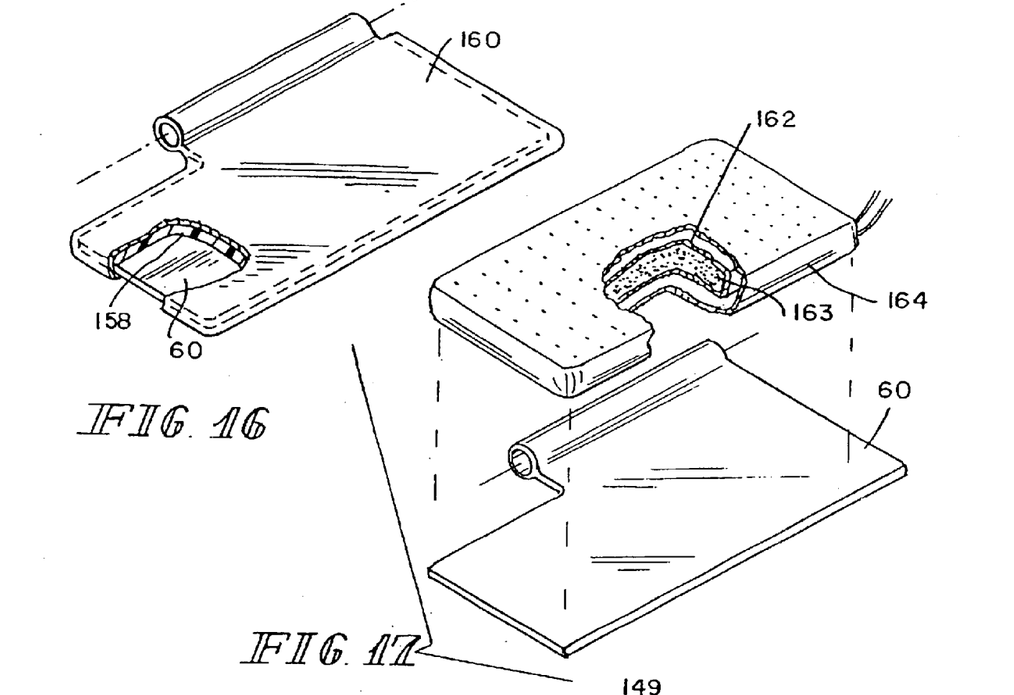
FIGS. 16 and 17 illustrate cushions configured to be located over the panels of the patient support surface.

Each of the panels 58–65 of patient support surface 50 is covered with a pressure reducing surface such as foam 158, etc., and a cover 160 as shown in FIG. 16. FIG. 17 illustrates an elastic material 162 such as Spandex which is filled with styrofoam beads 163 or other material. This elastic material 162 is illustratively placed within an outer cover 164 which has a controlled air leakage and which holds its shape for a predetermined amount of time. The outer cover 164 permits the inner elastic bag 162 of styrofoam beads 163 to be conformed to the shape of the patient. In one embodiment, the outer cover 164 or the inner bag 162 is formed to include a heating element made from, for instance, a resistive heating element such as Gorix™ material. A controller (not shown) is coupled to the heating element. The heating material is used to warm the patient on the patient support surface 50. Various combinations of the bags 162 and 164 positioned over foam or contoured foam may be used on each section 58–65 of the patient support surface 50.

A movable transfer surface 170 is illustratively coupled to base 12 as shown in FIGS. 1 and 2. Surface 170 is lifted upwardly when the patient support surface 50 is loaded onto or removed from bed 10 by a suitable lifting mechanism 172 coupled between the surface 170 and base 12. Lifting mechanism 172 is any conventional lifting mechanism such as a scissors lift linkage, parallelogram linkage, etc. Surface 170 moves upwardly in the direction of arrow 174 in FIG. 2 and can support the patient support surface 50 if the latch mechanisms should fail. If desired, the surface 170 can remain in its upwardly lifted, elevated position below patient support surface 50, except for during rotation of the patient, when surface 170 must be lowered. As discussed above, the surface 170 may be used to open latches 81, 82 and 84.

Figure 18:
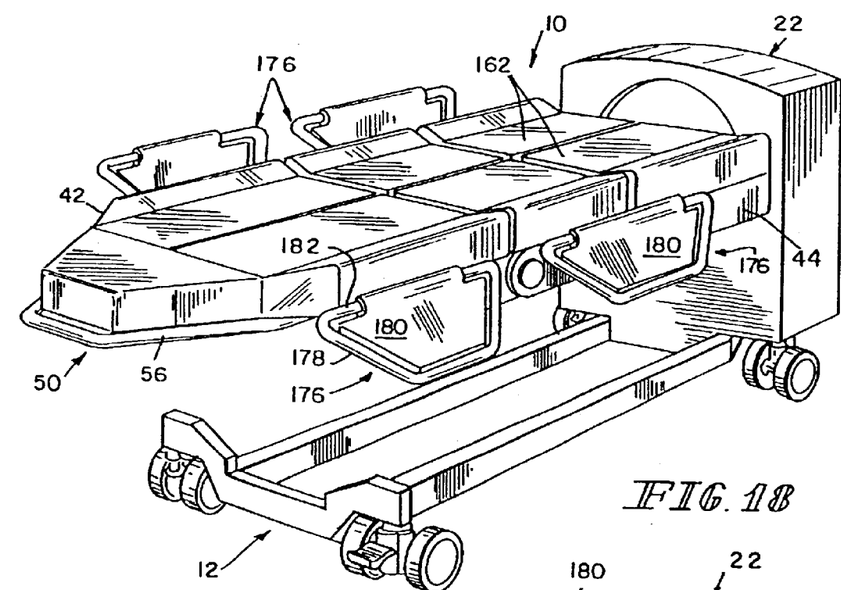
FIG. 18 is a perspective view of the proning bed of the present invention with siderails mounted to the first and second support arms.
Figure 19:
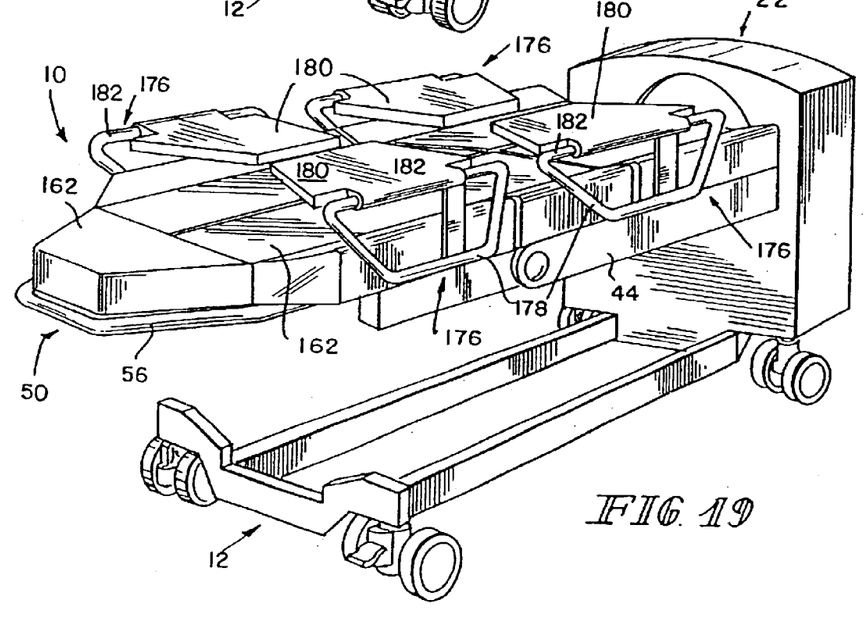
FIG. 19 is a perspective view of the bed of FIG. 18 illustrating portions of the siderails being positioned over the patient support surface to provide a proning support surface for the proning bed.

When it is desired to rotate the patient in order to move the patient to a prone position, a suitable proning surface is placed over the patient. The proning surface is coupled to side arms 42 and 44. FIGS. 18 and 19 illustrate one embodiment of the proning support surface. In this embodiment, outwardly blocking siderails 176 are pivotably coupled to support arms 42 and 44. The siderails 176 include an outer frame member 178 and a movable inner member or center portion 180 rotatably coupled to a top bar or rail 182 of the frame member 178. The siderails 176 are movable to a lowered position illustrated by the siderails coupled to support arm 44 in FIG. 18. The siderails 176 are also movable to an elevated position illustrated by the other siderails 176 coupled to arm 42 in FIG. 18. After the siderails 176 are in the elevated position, center portions 180 are each pivoted from a first position substantially within a plane defined by the frame member 178 to a second position substantially perpendicular to the first position. In the second positions, the center portions 180 extend over a patient on the patient support surface 50 as shown in FIG. 19 to provide a prone support surface. A suitable surface for supporting the patient's head and body (not shown) is coupled to the portions 180 above the patient. Latches may be provided, if necessary to secure the portions 180 located on opposite sides of the bed 10 together for proning.

Although the invention has been described in detail with reference to certain illustrated embodiments, variations and modifications exist within the scope and spirit of the invention as described and defined in the following claims.

What is claimed is:

1. A patient support comprising: a base;
a support assembly coupled to the base;
a patient support surface supported by the support assembly;
a plurality of siderails supported by the support assembly, each of the plurality of siderails being configured to move between a lowered position and an elevated position, wherein each of the plurality of siderails is configured to block egress from the patient support surface in the elevated position; and
the plurality of siderails each including a frame member and a movable member coupled to the frame member, the movable member being configured to move relative to the frame member to a position directly above the patient support surface when the siderail is in the elevated position.

2. The patient support of claim 1, wherein the support assembly includes first and second support arms located above the base, the plurality of siderails being coupled to the first and second support arms.

3. The patient support of claim 1, wherein the frame member of each of the plurality of siderails includes a top rail, and the movable member is rotatably coupled to the top rail.

4. The patient support of claim 1, further comprising a transfer surface coupled to the base, the transfer surface being movable from a lowered position to an elevated position located adjacent the support assembly.

5. The patient support of claim 1, wherein the patient support is supported for rotation about a longitudinal axis.

6. The patient support of claim 5, wherein the base includes a first end and a second end, the support assembly is coupled to the base adjacent to the first end, and the support assembly includes a rotatable drive mechanism configured to rotate the patient support surface about the longitudinal axis.

7. The patient support of claim 1, wherein the movable members of the siderails define at least a portion of a second patient support surface when positioned directly above the patient support surface.

8. The patient support of claim 1, wherein the movable members of the siderails are held in a locked condition when positioned directly above the patient support surface.

9. The patient support of claim 8, wherein at least one latch holds the movable members in the locked condition.

10. The patient support of claim 1, wherein the support assembly is coupled to the base in a cantilevered fashion.

11. A patient support comprising:
a base;
a support assembly coupled to the base, the support assembly includes first and second support arms located above the base;
a patient support surface coupled to the support assembly;
a plurality of siderails coupled to the first and second support arms of the support assembly, each of the plurality of siderails being configured to move between a lowered position and an elevated position, the plurality of siderails each including a frame member and a movable member coupled to the frame member, the movable member being configured to move relative to the frame member to a position directly above the patient support surface when the siderail is in the elevated position; and
a plurality of latch mechanisms coupled to the first and second support arms, the patient support surface being configured to be coupled to the first and second support arms by the plurality of latch mechanisms, and the patient support surface being removable from the first and second support arms to permit transfer of a patient to and from the patient support on the patient support surface.

12. The patient support of claim 11, wherein the patient support surface includes an outer frame configured to be coupled to the plurality of latch mechanisms to secure the patient support surface to the first and second support arms.

13. The patient support of claims 11, wherein the frame member of each of the plurality of siderails includes a top rail, and the movable member is rotatably coupled to the top rail.

14. The patient support of claim 11, wherein the support assembly is coupled to the base in a cantilevered fashion.

15. A patient support comprising:
a base;
a support assembly coupled to the base;
a patient support surface coupled to the support assembly;
a plurality of siderails coupled to the support assembly, each of the plurality of siderails being configured to move between a lowered position and an elevated position; and
the plurality of siderails each including a frame member and a movable member coupled to the frame member, the movable member being configured to move relative to the frame member to a position directly above the patient support surface when the siderail is in the elevated position, wherein the patient support surface is supported for rotation about a longitudinal axis, the movable members of the siderails forming a proning surface configured to support a patient in a prone position when the patient support surface is rotated 180° about the longitudinal axis.

16. The patient support of claim 15, wherein the base includes a first end and a second end, the support assembly is coupled to the base adjacent to the first end, and the support assembly includes a rotatable drive mechanism configured to rotate the patient support surface about the longitudinal axis.

17. The patient support of claim 16, wherein the support assembly is coupled to the base in a cantilevered fashion.

18. A patient support comprising:
a base;
a support assembly coupled to the base;
a patient support surface coupled to the support assembly;
a plurality of siderails coupled to the support assembly, each of the plurality of siderails being configured to move between a lowered position and an elevated position; and
the plurality of siderails each including a frame member and a movable member coupled to the frame member, the movable member being configured to move relative to the frame member to a position directly above the patient support surface when the siderail is in the elevated position, wherein the patient support surface includes at least one hinge to permit articulation of the patient support surface, the hinge being selectively lockable to hold the patient support surface in a generally planar orientation.

19. The patient support of claim 18, wherein the support assembly is coupled to the base in a cantilevered fashion.

20. A proning bed having an associated medical line, the proning bed comprising:

a base;

a support assembly coupled to the base, the support assembly having a longitudinal end;

a patient support surface coupled to the support assembly, the patient support surface being configured to support a patient in a supine position and to rotate about a longitudinal axis;

a proning surface coupled to the support assembly and being configured to support the patient in a prone position when the patient support surface is rotated 180° about the longitudinal axis;

a plurality of siderails coupled to the support assembly, the plurality of siderails each including a portion which is movable over the patient support surface to form at least a portion of the proning surface; and a line management device coupled to the longitudinal end of the support assembly and adapted to route the medical line.

21. The proning bed of claim 20, wherein the support assembly includes first and second support arms located above the base, the plurality of siderails being coupled to the first and second support arms.

22. The proning bed of claim 20, wherein the base includes a first end and a second end, the support assembly is coupled to the base adjacent to the first end, and the support assembly includes a rotatable drive mechanism configured to rotate the patient support surface about the longitudinal axis.

23. The proning bed of claim 20, wherein each of the plurality of siderails includes a frame member having a top rail, and the movable portion is rotatably coupled to the top rail.

24. The patient support of claim 20, wherein the line management device includes a base member including apertures for receiving the medical line.

25. The patient support of claim 20, wherein the line management device includes a base member including notches for receiving the medical lines.

26. The proning bed of claim 20, wherein the longitudinal end is a head end.

27. A proning bed comprising:

a base;

a support assembly coupled to the base;

a patient support surface coupled to the support assembly, the patient support surface being configured to support a patient in a supine position and to rotate about a longitudinal axis;

a proning surface coupled to the support assembly and being configured to support the patient in a prone position when the patient support surface is rotated 180° about the longitudinal axis; and a plurality of siderails coupled to the support assembly, the plurality of siderails each including a portion which is movable over the patient support surface to form at least a portion of the proning surface, wherein the frame member of each of the plurality of siderails is configured to move between a lowered position and an elevated position.

28. The proning bed of claim 27, wherein the support assembly is coupled to the base in a cantilevered fashion.

29. A siderail for a patient support, the siderail comprising:

a frame member configured to be coupled to the patient support, the frame member including a rail; and a movable member rotatably coupled to the rail of the frame member, the movable member configured to move from a first position substantially within a plane defined by the frame member to a second position substantially parallel to and spaced above a patient support surface.

30. The siderail of claim 29, wherein the patient support surface is supported for rotation about a longitudinal axis, the movable members of the siderails forming a proning surface configured to support a patient in a prone position when the patient support surface is rotated 180° about the longitudinal axis.

31. The siderail of claim 29, wherein the frame member is configured to move between a lowered position and an elevated position.

32. The siderail of claim 29, wherein the moveable member is coupled to the frame member adjacent a first end of the moveable member.

33. A siderail for a patient support including a patient support surface, the siderail comprising:

a first portion adapted to be coupled to the patient support and configured for movement between a lowered position and an elevated position, the first portion being substantially perpendicular to the patient support surface in the elevated position and a second portion including a support surface, the second portion being coupled to the first portion for movement from a first position generally parallel to the first portion to a second position generally above the patient support surface of the patient support.

34. The siderail of claim 33, wherein the second portion is rotatably coupled to the first portion.

35. The siderail of claim 33, wherein the second portion defines at least a portion of a second patient support surface.

36. The siderail of claim 35, wherein the second portion is located on a first side of the first portion in the first position and on a second side of the first portion in the second position.

37. A patient support, comprising:

a base;

a support assembly coupled to the base and configured to be rotatable about a longitudinal axis;

a first patient support surface supported by the support assembly;

a plurality of siderails supported by the support assembly and movable between a lowered position and an elevated position, the siderails being substantially perpendicular to the first patient support surface in the elevated position; and a second patient support surface supported by the plurality of siderails, wherein the first patient support surface is configured to support a patient in the supine position and the second patient support surface is configured to support the patient in the prone position.

38. The patient support of claim 37, wherein each of the plurality of siderails includes a first portion coupled to the support assembly and a second portion movable relative to the first portion, the second portion defining a portion of the second patient support.

39. The patient support of claim 37, wherein the plurality of siderails each includes a top rail and the second patient support surface is coupled to the top rail.

40. The patient support of claim 37, wherein the support assembly is coupled to the base in a cantilevered fashion.

41. A patient support having an associated medical line, the patient support comprising:

a base;

a support assembly coupled to the base and rotatable about a longitudinal axis, the support assembly having a longitudinal end;

a first patient support surface supported by the support assembly; and a line management device supported by the support assembly at the longitudinal end of the support assembly and adapted to route the medical line.

42. The patient support of claim 41, further comprising a second patient support surface supported by the support assembly, wherein the first patient support surface is configured to support a patient in the supine position and the second patient support surface is configured to support the patient in the prone position.

43. The patient support of claim 41, wherein the line management device includes a base member including apertures for receiving the medical line.

44. The patient support of claim 41, wherein the line management device includes a base member including notches for receiving the medical lines.

45. The patient support of claim 41, wherein the longitudinal end is a head end.

* * * * *